United States Patent [19]

Remers

[11] Patent Number: 4,746,746

[45] Date of Patent: May 24, 1988

[54] MITOMYCIN ANALOGS

[75] Inventor: William A. Remers, Tucson, Ariz.

[73] Assignee: University Patents, Inc., Westport, Conn.

[21] Appl. No.: 757,194

[22] Filed: Jul. 22, 1985

Related U.S. Application Data

[63] Continuation of Ser. No. 464,612, Feb. 7, 1983, abandoned.

[51] Int. Cl.⁴ .................. C07D 487/12; A61K 31/40; A61K 31/425
[52] U.S. Cl. ..................... 548/159; 548/212; 548/214; 548/255; 548/266; 548/267; 548/336; 548/422; 546/199
[58] Field of Search ............ 548/422, 159, 212, 214, 548/255, 266, 267, 336, 271

[56] References Cited

PUBLICATIONS

Burger, ed., *Medicinal Chemistry*, 2nd ed., Interscience Pub. N.Y. (1960) p. 40.

*Primary Examiner*—Donald G. Daus
*Assistant Examiner*—William A. Teoli, Jr.
*Attorney, Agent, or Firm*—Marshall, O'Toole, Gerstein, Murray & Bicknell

[57] ABSTRACT

Novel methods for treatment of neoplastic disease states in animals, which methods comprise administering a therapeutically effective amount of a compound of the formula IIIa,

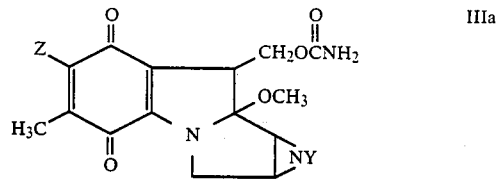

wherein: Y is hydrogen or lower alkyl; and Z is
 an hydroxy substitited 1-pyrrolidinyl radical, or
 a lower alkyl substituted piperidyl radical, or
 a 1-piperazinyl radical or an acetamino, acetyl, carbamido, cyano, carboxy lower alkylamino, di-lower alkoxy, nitro, sulfamyl, or lower alkyl substituted anilino radical, or
 a radical of the formula,

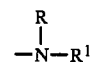

wherein R is hydrogen or lower alkyl and $R^1$ is a nitrogen containing heterocyclic radical selected from the group consisting of amino substituted triazolyl, lower alkyl substituted isothiazolyl, benzothiazolyl, and nitro and halo substituted derivatives of benzothiazolyl, or $R^1$ is
 a substituted lower alkyl radical selected from the group consisting of amino lower alkyl, lower alkylamino lower alkyl, hydroxy lower alkylamino lower alkyl, hydroxy lower alkoxy lower alkyl, imidazolyl lower alkyl, nitro substituted imidazolyl lower alkyl, mono- and di-hydroxy phenyl lower alkyl, nitro substituted pyridylamino lower alkyl, piperazinyl lower alkyl, and pyridyl ethyl.

10 Claims, No Drawings

MITOMYCIN ANALOGS

This application is a continuation, of application Ser. No. 464,612, filed 2/7/83 now abandoned.

BACKGROUND

The present invention relates generally to antibiotic mitosane compounds and to their use in the treatment of neoplastic disease states in animals.

The disclosures of my U.S. Pat. No. 4,268,676; my co-pending U.S. patent application Ser. No. 206,529 filed Nov. 13, 1980; and my co-pending U.S. patent application Ser. No. 264,187 filed May 15, 1981, are specifically incorporated by reference herein to the extent that they may provide essential and nonessential material relating to the present invention.

Briefly summarized, said U.S. Pat. No. 4,268,676 and co-pending application Ser. No. 206,529 set forth a statement of the background of the ongoing search in the art for new and useful compounds which are structurally related to the mitomycins, which possess antibiotic activity, which have low toxicity and which display a substantial degree of antitumor activity in animals. More particularly, they disclose new compounds of the formula I,

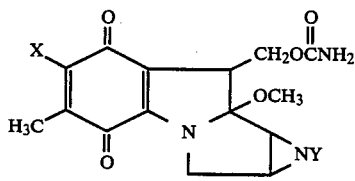

wherein: Y is hydrogen or lower alkyl; and X is a thiazolamino radical, a furfurylamino radical or a radical of the formula,

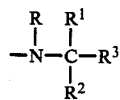

in which R, $R^1$ and $R^2$ are the same or different and selected from the group consisting of hydrogen and lower alkyl, and $R^3$ is selected from the group consisting of lower alkenyl, halo-lower alkenyl, lower alkynyl, lower alkoxycarbonyl, thienyl, formamyl, tetrahydrofuryl and benzene sulfonamide.

Said U.S. patent and pending application also disclose novel methods for treatment of neoplastic disease states in animals, which methods comprise administering a therapeutically effective amount of a compound of the formula, Ia,

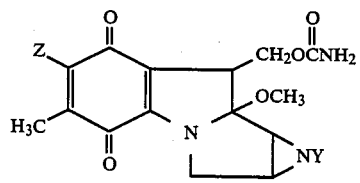

wherein: Y is hydrogen or lower alkyl; and Z is a thiazolamino radical, a furfurylamino radical, a cyclopropylamino radical, a pyridylamino radical, or a radical of the formula,

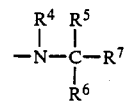

in which $R^4$, $R^5$, and $R^6$ are the same or different and selected from the group consisting of hydrogen and lower alkyl, and $R^7$ is selected from the group consisting of lower alkenyl, halo-lower alkenyl, lower alkynyl, lower alkoxycarbonyl, halo-lower alkyl, hydroxy-lower alkyl, pyridyl, thienyl, formamyl, tetrahydrofuryl, benzyl, and benzene sulfonamide.

Co-pending U.S. patent application Ser. No. 264,187 also discloses compounds with a substantial degree of antitumor activity in animals of the following formula IIa,

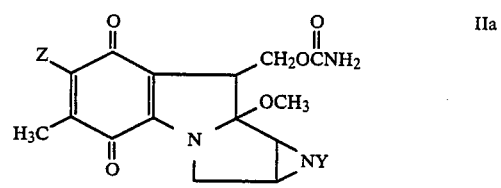

wherein: Y is hydrogen or lower alkyl; and Z is a lower alkoxy substituted quinolinylamino radical, a cyano substituted pyrazolylamino radical or a mono- or di-lower alkyl substituted thiazolamino radical, or a nitrogen-containing heterocyclic radical selected from the group consisting of 1-pyrrolinyl, 1-indolinyl, N-thiazolidinyl, N-morpholinyl, 1-piperazinyl, and N-thiomorpholinyl radicals, or a cyano, phenyl, carboxamido or lower alkoxycarbonyl substituted 1-aziridinyl radical, or a lower alkyl, formyl or acetylphenyl substituted 1-piperazinyl radical, or an hydroxy or piperidyl substituted 1-piperidyl radical, or a lower alkoxy, amino or halo substituted pyridylamino radical, or a carboxamido, mercapto or methylenedioxy substituted anilino radical, or a radical of the formula,

wherein R is hydrogen or lower alkyl and R' is a nitrogen-containing heterocyclic radical selected from the group consisting of quinuclidinyl, pyrazolyl, 1-triazolyl, isoquinolinyl, indazolyl, benzoxazolyl, thiadiazolyl and benzothiadiazolyl, and lower alkyl and halo substituted derivatives thereof, or a butyrolactonyl radical, or an adamantyl radical, or a mono-lower alkoxy substituted phenyl radical, or a substituted lower alkyl radical selected from the group consisting of mercapto lower alkyl, carboxy lower alkyl, mono-, di- and tri-lower alkoxy lower alkyl, lower alkyl thio lower alkyl and lower alkoxycarbonyl substituted derivatives thereof, cyano lower alkyl, mono-, di- and trilower alkoxy phenyl lower alkyl, phenyl cyclo lower alkyl, 1-pyrrolidinyl lower alkyl, N-lower alkyl pyrrolidinyl lower alkyl, N-morpholinyl lower alkyl, and lower dialkylamino lower alkyl.

Also pertinent to the background of the present invention are the following references: Cosulich, et al., U.S. Pat. No. 3,332,944; Matsui, et al., U.S. Pat. No. 3,410,867; Nakano, et al., U.S. Pat. No. 4,231,936; Matsui, et al., U.S. Pat. No. 3,429,894; Remers, U.S. Pat. No. 4,268,676; Matsui, et al., U.S. Pat. No. 3,450,705; Matsui, et al., U.S. Pat. No. 3,514,452; and Imai, et al., Gann, 71, pp. 560–562 (1980).

BRIEF SUMMARY

According to the present invention, there are provided novel compounds of the formula, III,

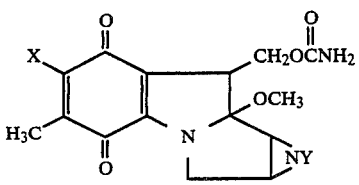

wherein: Y is hydrogen or lower alkyl; and X is
an hydroxy substituted 1-pyrrolidinyl radical, or
a lower alkyl substituted piperidyl radical, or
an acetamino, acetyl, carbamido, cyano, carboxy lower alkylamino, di-lower alkoxy, nitro, or sulfamyl substituted anilino radical, or
a radical of the formula,

wherein R is hydrogen or lower alkyl and $R^1$ is a nitrogen containing heterocyclic radical selected from the group consisting of amino substituted triazolyl, lower alkyl substituted isothiazolyl, benzothiazolyl, and nitro and halo substituted derivatives of benzothiazolyl, or $R^1$ is
a substituted lower alkyl radical selected from the group consisting of amino lower alkyl, lower alkylamino lower alkyl, hydroxy lower alkylamino lower alkyl, hydroxy lower alkoxy lower alkyl, imidazolyl lower alkyl, nitro substituted imidazolyl lower alkyl, mono- and di-hydroxy phenyl lower alkyl, nitro substituted pyridylamino lower alkyl, and piperazinyl lower alkyl.

Also provided according to the invention are novel methods for treatment of neoplastic disease states in animals, which methods comprise administering a therapeutically effective amount of a compound of the formula, IIIa,

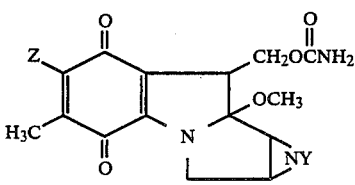

wherein: Y is hydrogen or lower alkyl; and Z is
an hydroxy substituted 1-pyrrolidinyl radical, or
a lower alkyl substituted piperidyl radical, or
a 1-piperazinyl radical or an acetamino, acetyl, carbamido, cyano, carboxy lower alkylamino, di-lower alkoxy, nitro, sulfamyl, or lower alkyl substituted anilino radical, or
a radical of the formula,

wherein R is hydrogen or lower alkyl and $R^1$ is a nitrogen containing heterocyclic radical selected from the group consisting of amino substituted triazolyl, lower alkyl substituted isothiazolyl, benzothiazolyl, and nitro and halo substituted derivatives of benzothiazolyl, or $R^1$ is
a substituted lower alkyl radical selected from the group consisting of amino lower alkyl, lower alkylamino lower alkyl, hydroxy lower alkylamino lower alkyl, hydroxy lower alkoxy lower alkyl, imidazolyl lower alkyl, nitro substituted imidazolyl lower alkyl, mono- and di-hydroxy phenyl lower alkyl, nitro substituted pyridylamino lower alkyl, piperazinyl lower alkyl, and pyridyl ethyl.

Unless otherwise indicated, the term "lower", applied to "alkyl" radicals shall designate such straight or branched chain radicals as to include from one to six carbon atoms. By way of illustration, "lower alkyl" shall mean and include methyl, ethyl, propyl, butyl, pentyl and hexyl radicals as well as isopropyl radicals, t-butyl radicals and the like. Similarly, "lower" as applied to "alkoxy" shall designate a radical having one to six carbon atoms.

It will be apparent that the compounds of formula III are all comprehended by the specifications of formula IIIa. Put another way, all the novel antibiotic mitomycin derivatives of formula III are useful in practice of the novel antineoplastic therapeutic methods which involve administration of compounds of formula IIIa.

Mitomycin derivatives of the invention are prepared by the reaction of mitomycin A with the appropriately selected amine compounds. The N-alkylmitomycin (e.g., N-methylmitomycin) derivatives are similarly prepared by the reaction of a selected amine with N-alkylmitomycin A prepared from mitomycin C, e.g., according to the methods generally disclosed in Cheng, et al., *J.Med.Chem.*, 20, No. 6, 767–770 (1977). The preparative reactions generally yield the desired product as a crystalline solid which is readily soluble in alcohol.

Therapeutic methods of the invention comprehend the administration of effective amounts of one or more of the compounds of formula IIIa, as an active ingredient, together with desired pharmaceutically acceptable diluents, adjuvants and carriers, to an animal suffering from a neoplastic disease state. Unit dosage forms of compounds administered according to the methods of the invention may range from about 0.001 to about 5.0 mg and preferably from about 0.004 to about 1.0 mg, of the compounds. Such unit dosage quantities may be given to provide a daily dosage of from about 0.1 to about 100 mg per kg, and preferably from about 0.2 to about 51.2 mg per kg, of body weight of the animal treated. Parenteral administration, and especially intraperitoneal administration, is the preferred route for practice of the inventive methods.

Other aspects and advantages of the present invention will become apparent upon consideration of the following description.

DESCRIPTION OF INVENTION

The following Examples 1 through 32, describing preparation of certain presently preferred compounds according to the invention, are for illustrative purposes only and are not to be construed as limiting the invention. Unless otherwise indicated, all reactions were carried out at room temperature (20° C.), without added heat. Unless otherwise indicated, all thin layer chromatographic (TLC) procedures employed to check the progress of reactions involved the use of a pre-coated silica-gel plate and a mixture of methanol and chloroform (2:8 by volume) as a developing solvent.

EXAMPLE 1

1,1a,2,8,8a,8b-Hexahydro-8-(hydroxymethyl)-8a-methoxy-5-methyl-6-(3-hydroxy-1-pyrrolidinyl)-azirino[2',3':3,4]pyrrolo[1,2-a]indole-4,7-dione carbamate A solution of mitomycin A (50 mg) in 6 ml of anhydrous methanol was treated with 3-pyrrolidinol (13 mg) under nitrogen at room temperature. When thin-layer chromatography on silica gel (2:8 methanol-chloroform as solvent) showed that starting material no longer was present, the mixture was filtered and evaporated under reduced pressure. The residue was purified by preparative thinlayer chromatography using the same solvent system. This procedure gave 23 mg (40% yield) of the desired product having a melting point of 82°–85° C. (decomposition) and providing the following analysis:

NMR (DMSO-$d_6$, TS): 'δ' values in ppm. Absence of the 6-methoxy peak at 4.02 and the appearance of new peaks at 1.6–2.2 (m,2), 2.8–3.1 (broad s,5) and 4.0–4.3 (m,1).

EXAMPLE 2

1,1a,2,8,8a,8b-Hexahydro-8-(hydroxymethyl)-8a-methoxy-5-methyl-6-(3-methylpiperdyl)-azirino[2',3':3,4]pyrrolo[1,2-a]indole-4,7-dione carbamate This compound was prepared by the procedure described in Example 1. From 70 mg of mitomycin A and 200 mg of 3-methyl piperdine was obtained 46 mg (55% yield) of the desired product having a melting point of 75°–88° C. (decomposition) and providing the following analysis:

NMR (CDCl$_3$, TS): 'δ' values in ppm. Absence of the 6-methoxy peak at 4.02 and the appearance of new peaks at 0.85 (d,3), 1.10–2.15 (m,5) and 2.15–3.32 (m,4).

EXAMPLE 3

1,1a,2,8,8a,8b-Hexahydro-8-(hydroxymethyl)-8a-methoxy-5-methyl-6-(1-piperazinyl)-azirino[2',3':3,4]pyrrolo[1,2-a]indole-4,7-dione carbamate This compound was prepared by the procedure described in Example 1. From 60 mg of mitomycin A and 30 mg of anhydrous piperazine was obtained 23 mg (34% yield) of the desired product having a melting point greater than 200° C. (decomposition) and providing the following analysis:

NMR (DMSO-$d_6$, TS): 'δ' values in ppm. Absence of the 6-methoxy peak at 4.02 and the appearance of new peaks at 1.9 (broad s,1) and 2.9 (s,8).

EXAMPLE 4

1,1a,2,8,8a,8b-Hexahydro-8-(hydroxymethyl)-8a-methoxy-5-methyl-6-[4-(acetylamino)anilino]-azirino[2',3':3,4]pyrrolo[1,2-a]indole-4,7-dione carbamate This compound was prepared by the procedure described in Example 1. From 100 mg of mitomycin A and excess 4-(acetylamino)aniline was obtained 102 mg (76% yield) of the desired product having a melting point of 143°–145° C. (decomposition) and providing the following analysis:

NMR (CDCl$_3$, TS): 'δ' values in ppm. Absence of the 6-methoxy peak at 4.02 and the appearance of new peaks at 2.1 (s,3), 7.4 (d,2), 7.6 (s,1) and 8.9–9.3 (s,1).

EXAMPLE 5

1,1a,2,8,8a,8b-Hexahydro-8-(hydroxymethyl)-8a-methoxy-5-methyl-6-[3-(acetylamino)anilino]-azirino[2',3':3,4]pyrrolo[1,2-a]indole-4,7-dione carbamate This compound was prepared by the procedure described in Example 1, except that a small amount of solid potassium carbonate was added. From 70 mg of mitomycin A and 150 mg of 3-(acetylamino)aniline was obtained 67 mg (72% yield) of the desired product having a melting point of 140°–143° C. (decomposition) and providing the following analysis:

NMR (Acetone-$d_6$, TS): 'δ' values in ppm. Absence of the 6-methoxy peak at 4.02 and the appearance of new peaks at 2.1 (s,3), 6.7–7.5 (m,4), 8.0 (broad s,1) and 9.3 (s,1).

EXAMPLE 6

1,1a,2,8,8a,8b-Hexahydro-8-(hydroxymethyl)-8a-methoxy-5-methyl-6-(4-acetylanilino)-azirino[2',3':3,4]pyrrolo[1,2-a]indole-4,7-dione carbamate This compound was prepared by the procedure described in Example 1, except that a small amount of solid potassium carbonate was added. From 70 mg of mitomycin A and 510 mg of 4-acetylaniline was obtained 25 mg (28% yield) of the desired product having a melting point of 103°–104° C. (decomposition) and providing the following analysis:

NMR (CDCl$_3$, TS): 'δ' values in ppm. Absence of the 6-methoxy peak at 4.02 and the appearance of new peaks at 2.1 (s,3), 6.6(d,2), 7.3 (d,2) and 7.0–7.3 (broad s,1).

EXAMPLE 7

1,1a,2,8,8a,8b-Hexahydro-8-(hydroxymethyl)-8a-methoxy-5-methyl-6-[4-(1-ureido)anilino]-azirino[2',3':3,4]pyrrolo[1,2-a]indole-4,7-dione carbamate This carbamido-substituted compound was prepared by the procedure described in Example 1. From 50 mg of mitomycin A and 227 mg of 4-(1-ureido)aniline was obtained 49 mg (67% yield) of the desired product having a melting point of 93°–95° C. (decomposition) and providing the following analysis:

NMR (CDCl$_3$, TS): 'δ' values in ppm. Absence of the 6-methoxy peak at 4.02 and the appearance of new peaks at 5.03 (s,2), 6.9 (d,2), 7.3 (d,2), 8.0 (s,1) and 8.4 (s,1).

EXAMPLE 8

1,1a,2,8,8a,8b-Hexahydro-8-(hydroxymethyl)-8a-methoxy-5-methyl-6-(4-cyanoanilino)-azirino[2',3':3,4-]pyrrolo[1,2-a]indole-4,7-dione carbamate This compound was prepared by the procedure described in Example 1, except that a small amount of solid potassium carbonate was added. From 70 mg of mitomycin A and 472 mg of 4-aminobenzonitrile was obtained 23 mg (24% yield) of the desired product having a melting point of 124°–126° C. (decomposition) and providing the following analysis:

NMR (CDCl$_3$, TS): 'δ' values in ppm. Absence of the 6-methoxy peak at 4.02 and the appearance of new peaks at 6.6 (d,2), 7.4 (d,2) and 7.0–7.3 (broad s,1).

EXAMPLE 9

1,1a,2,8,8a,8b-Hexahydro-8-(hydroxymethyl)-8a-methoxy-5-methyl-6-(3-cyanoanilino)-azirino[2',3':3,4-]pyrrolo[1,2-a]indole-4,7-dione carbamate This compound was prepared by the procedure described in Example 1, except that a small amount of solid potassium carbonate was added. From 71 mg of mitomycin A and 500 mg of 3-aminobenzonitrile was obtained 30 mg (34% yield) of the desired product having a melting point of 97°–98° C. (decomposition) and providing the following analysis:

NMR (CDCl$_3$, TS): 'δ' values in ppm. Absence of the 6-methoxy peak at 4.02 and the appearance of new peaks at 7.2–7.8 (m,4).

EXAMPLE 10

1,1a,2,8,8a,8b-Hexahydro-8-(hydroxymethyl)-8a-methoxy-5-methyl-6-[4-(N-glycyl)anilino]-azirino[2',3':3,4]pyrrolo[1,2-a]indole-4,7-dione carbamate This compound was prepared by the procedure described in Example 1. From 50 mg of mitomycin A and 249 mg of 4-(N-glycyl)aniline was obtained 62 mg (90% yield) of the desired product having a melting point of 83°–85° C. (decomposition) and providing the following analysis:

NMR (DMSO-d$_6$, TS): 'δ' values in ppm. Absence of the 6-methoxy peak at 4.02 and the appearance of new peaks at 3.1 (s,2), 6.3–6.6 (broad s,2), 6.6–6.8 (broad s,2) and 6.6–7.1 (broad s,2).

EXAMPLE 11

1,1a,2,8,8a,8b-Hexahydro-8-(hydroxymethyl)-8a-methoxy-5-methyl-6-(3,4-dimethoxyanilino)-azirino[2',3':3,4]pyrrolo[1,2-a]indole-4,7-dione carbamate This compound was prepared by the procedure described in Example 1. From 50 mg of mitomycin A and 229 mg of 3,4-dimethoxyaniline was obtained 61 mg (91% yield) of the desired product having a melting point of 114°–116° C. (decomposition) and providing the following analysis:

NMR (CDCl$_3$, TS): 'δ' values in ppm. Absence of the 6-methoxy peak at 4.02 and the appearance of new peaks at 3.8 (s,6), 6.3–6.9 (m,3) and 7.7 (s,1).

EXAMPLE 12

1,1a,2,8,8a,8b-Hexahydro-8-(hydroxymethyl)-8a-methoxy-5-methyl-6-(3,5-dimethoxyanilino)-azirino[2',3':3,4]pyrrolo[1,2-a]indole-4,7-dione carbamate This compound was prepared by the procedure described in Example 1. From 50 mg of mitomycin A and 229 mg of 3,5-dimethoxyaniline was obtained 60 mg (88% yield) of the desired product having a melting point of 98°–100° C. (decomposition) and providing the following analysis:

NMR (CDCl$_3$, TS): 'δ' values in ppm. Absence of the 6-methoxy peak at 4.02 and the appearance of new peaks at 3.8 (s,6), 5.9–6.4 (broad s,3) and 7.6 (s,1).

EXAMPLE 13

1,1a,2,8,8a,8b-Hexahydro-8-(hydroxymethyl)-8a-methoxy-5-methyl-6-(4-nitroanilino)-azirino[2',3':3,4-]pyrrolo[1,2-a]indole-4,7-dione carbamate This compound was prepared by the procedure described in Example 1, except that a small amount of solid potassium carbonate was added. From 70 mg of mitomycin A and 276 mg of 4-nitroaniline was obtained 16 mg (9% yield) of the desired product having a melting point of 132°–134° C. (decomposition) and providing the following analysis:

NMR (Acetone-d$_6$, TS): 'δ' values in ppm. Absence of the 6-methoxy peak at 4.02 and the appearance of new peaks at 6.9–7.3 (d,2), 7.4–7.9 (d,2) and 7.9–8.4 (broad s,1).

EXAMPLE 14

1,1a,2,8,8a,8b-Hexahydro-8-(hydroxymethyl)-8a-methoxy-5-methyl-6-(4-sulfamylanilino)-azirino[2',3':3,4]pyrrolo[1,2-a]indole-4,7-dione carbamate This compound was prepared by the procedure described in Example 1, except that a small amount of solid potassium carbonate was added. From 70 mg of mitomycin A and 688 mg of sulfanilamide was obtained 25 mg (26% yield) of the desired product having a melting point of 113°–115° C. (decomposition) and providing the following analysis:

NMR (CDCl$_3$, TS): 'δ' values in ppm. Absence of the 6-methoxy peak at 4.02 and the appearance of new peaks at 7.0 (d,2), 7.5 (s,1) and 7.9 (d,2).

EXAMPLE 15

1,1a,2,8,8a,8b-Hexahydro-8-(hydroxymethyl)-8a-methoxy-5-methyl-6-(4-methylanilino)-azirino[2',3':3,4-]pyrrolo[1,2-a]indole-4,7-dione carbamate This compound was prepared by the procedure described in Example 1. From 60 mg of mitomycin A and excess 4-methylaniline was obtained 63 mg (86% yield) of the desired product having a melting point of 113°–115° C. (decomposition) and providing the following analysis:

NMR (CDCl$_3$, TS): 'δ' values in ppm. Absence of the 6-methoxy peak at 4.02 and the appearance of new peaks at 2.3 (s,3), 6.5–7.3 (broad s,4) and 7.6 (broad s,1).

EXAMPLE 16

1,1a,2,8,8a,8b-Hexahydro-8-(hydroxymethyl)-8a-methoxy-5-methyl-6-(3-methylanilino)-azirino[2',3':3,4-]pyrrolo[1,2-a]indole-4,7-dione carbamate This compound was prepared by the procedure described in Example 1. From 70 mg of mitomycin A and 276 mg of 3-methylaniline was obtained 66 mg (78% yield) of the desired product having a melting point of 89°–91° C. (decomposition) and providing the following analysis:

NMR (CDCl$_3$, TS): 'δ' values in ppm. Absence of the 6-methoxy peak at 4.02 and the appearance of new peaks at 2.4 (s,3), 6.7–7.5 (m,4) and 7.8 (s,1).

EXAMPLE 17

1,1a,2,8,8a,8b-Hexahydro-8-(hydroxymethyl)-8a-methoxy-5-methyl-6-[(5-amino-1,2,4-triazol-3-yl)amino]-azirino[2',3':3,4]pyrrolo[1,2-a]indole-4,7-dione carbamate This compound was prepared by the procedure described in Example 1, except that a small amount of solid potassium carbonate was added. From 50 mg of mitomycin A and 30 mg of 3,5-diamino-1,2,4-triazole was obtained 13 mg (5.5% yield) of the desired product having a melting point of 117°–120° C. (decomposition) and providing the following analysis:

NMR (DMSO-d$_6$, TS): 'δ' values in ppm. Absence of the 6-methoxy peak at 4.02 and the appearance of a new peak at 5.37 (s,3).

EXAMPLE 18

1,1a,2,8,8a,8b-Hexahydro-8-(hydroxymethyl)-8a-methoxy-5-methyl-6-[(3-methylisothiazol-5-yl)amino]-azirino[2',3':3,4]pyrrolo[1,2-a]indole-4,7-dione carbamate This compound was prepared by the procedure described in Example 1, except that 0.5 ml of triethylamine was added. From 60 mg of mitomycin A and 30 mg of 5-amino3-methylisothiazole hydrochloride was obtained 4.5 mg (8.5% yield) of the desired product having a melting point of 87°–90° C. (decomposition) and providing the following analysis:

NMR (CDCl$_3$, TS): 'δ' values in ppm. Absence of the 6-methoxy peak at 4.02 and the appearance of new peaks at 2.3 (s,3), 6.1 (s,1) and 6.4 (s,1).

EXAMPLE 19

1,1a,2,8,8a,8b-Hexahydro-8-(hydroxymethyl)-8a-methoxy-5-methyl-6-[(2-benzothiazolyl)amino]-azirino[2',3':3,4]pyrrolo[1,2-a]indole-4,7-dione carbamate This compound was prepared by the procedure described in Example 1, except that a small amount of solid potassium carbonate was added. From 50 mg of mitomycin A and 25 mg of 2-aminobenzothiazole was obtained 12 mg (18% yield) of the desired product having a melting point of 82°–85° C. (decomposition) and providing the following analysis:

NMR (CDCl$_3$, TS): 'δ' values in ppm. Absence of the 6-methoxy peak at 4.02 and the appearance of new peaks at 7.1–8.0 (m,5).

EXAMPLE 20

1,1a,2,8,8a,8b-Hexahydro-8-(hydroxymethyl)-8a-methoxy-5-methyl-6-[(6-nitrobenzothiazol-2-yl)amino]-azirino[2',3':3,4]pyrrolo[1,2-a]indole-4,7-dione carbamate This compound was prepared by the procedure described in Example 1, except that a small amount of solid potassium carbonate was added. From 50 mg of mitomycin A and 30 mg of 2-amino-6-nitrobenzothiazole was obtained 20 mg (27% yield) of the desired product having a melting point of 86°–89° C. (decomposition) and providing the following analysis:

NMR (DMSO-d$_6$, TS): 'δ' values in ppm. Absence of the 6-methoxy peak at 4.02 and the appearance of new peaks at 6.9–8.3 (m,4).

EXAMPLE 21

1,1a,2,8,8a,8b-Hexahydro-8-(hydroxymethyl)-8a-methoxy-5-methyl-6-[(4-chlorobenzothiazol-2-yl)amino]-azirino[2',3':3,4]pyrrolo[1,2-a]indole-4,7-dione carbamate This compound was prepared by the procedure described in Example 1, except that a small amount of solid potassium carbonate was added. From 150 mg of mitomycin A and 27 mg of 2-amino-chlorobenzothiazole was obtained 30 mg (14% yield) of the desired product having a melting point of 89°–91° C. (decomposition) and providing the following analysis:

NMR (CDCl$_3$, TS): 'δ' values in ppm. Absence of the 6-methoxy peak at 4.02 and the appearance of new peaks at 7.1–8.0 (broad s,4).

EXAMPLE 22

1,1a,2,8,8a,8b-Hexahydro-8-(hydroxymethyl)-8a-methoxy-5-methyl-6-[(2-aminoethyl)amino]-azirino[2',3':3,4]pyrrolo[1,2-a]indole-4,7-dione carbamate This compound was prepared by the procedure described in Example 1, except that the solvent was dichloromethane. From 50 mg of mitomycin A and 10 mg of 1,2-diaminoethane was obtained 35 mg (65% yield) of the desired product having a melting point of 202°–205° C. (decomposition) and providing the following analysis:

NMR (CDCl$_3$, TS): 'δ' values in ppm. Absence of the 6-methoxy peak at 4.02 and the appearance of new peaks at 1.5 (broad s,2) and 3.5 (broad s,4).

EXAMPLE 23

1,1a,2,8,8a,8b-Hexahydro-8-(hydroxymethyl)-8a-methoxy-5-methyl-6-[methyl(2-methylaminoethyl)amino]-azirino[2',3':3,4]pyrrolo[1,2-a]indole-4,7-dione carbamate This compound was prepared by the procedure described in Example 1, except that a small amount of solid potassium carbonate was added. From 50 mg of mitomycin A and 25 mg of sym-dimethylethylenediamine was obtained 28 mg (50% yield) of the desired product having a melting point of 99°–101° C. (decomposition) and providing the following analysis:

NMR (CDCl$_3$, TS): 'δ' values in ppm. Absence of the 6-methoxy peak at 4.02 and the appearance of new peaks at 1.3 (s,1), 2.5 (s,6), and 2.7 (s,4).

EXAMPLE 24

1,1a,2,8,8a,8b-Hexahydro-8-(hydroxymethyl)-8a-methoxy-5-methyl-6-[2-(2-hydroxyethylamino)ethylamino]-azirino[2',3':3,4]pyrrolo[1,2-a]indole-4,7-dione carbamate This compound was prepared by the procedure described in Example 1, except that the solvent was dichloromethane. From 50 mg of mitomycin A and 18 mg of 2-(2-aminoethylamino)ethanol was obtained 35 mg (58% yield) of the desired product having a melting point of 115°–118° C. (decomposition) and providing the following analysis:

NMR (CDCl$_3$, TS): 'δ' values in ppm. Absence of the 6-methoxy peak at 4.02 and the appearance of new peaks at 2.7 (broad s,7) and 3.7 (t,3).

EXAMPLE 25

1,1a,2,8,8a,8b-Hexahydro-8-(hydroxymethyl)-8a-methoxy-5-methyl-6-[2-(2-hydroxyethoxy)ethylamino]-azirino[2',3':3,4]pyrrolo[1,2-a]indole-4,7-dione carbamate This compound was prepared by the procedure described in Example 1, except that the solvent was dichloromethane. From 60 mg of mitomycin A and 20 mg of 2-(2-aminoethoxy)ethanol was obtained 30 mg (42% yield) of the desired product having a melting point of 99°–102° C. (decomposition) and providing the following analysis:

NMR (CDCl$_3$, TS): 'δ' values in ppm. Absence of the 6-methoxy peak at 4.02 and the appearance of new peaks at 3.3–3.9 (broad s,9) and 6.4–6.8 (broad s,1).

EXAMPLE 26

1,1a,2,8,8a,8b-Hexahydro-8-(hydroxymethyl)-8a-methoxy-5-methyl-6-[2-(4-imidazolyl)ethylamino]-azirino[2',3':3,4]pyrrolo[1,2-a]indole-4,7-dione carbamate This compound was prepared by the procedure described in Example 1, except that 128 mg of sodium methoxide was added. From 70 mg of mitomycin A and 368 mg of histamine dihydrochloride was obtained 61 mg (71% yield) of the desired product having a melting point of 72°–73° C. (decomposition) and providing the following analysis:

NMR (DMSO-d$_6$, TS): 'δ' values in ppm. Absence of the 6-methoxy peak at 4.02 and the appearance of new peaks at 3.0–3.27 (m,4), 7.5 (s,1), 8.0–8.7 (broad s,2) and 8.1 (s,1).

EXAMPLE 27

1,1a,2,8,8a,8b-Hexahydro-8-(hydroxymethyl)-8a-methoxy-5-methyl-6-[(2-nitro-1-imidazolyl)ethylamino]-azirino[2',3':3,4]pyrrolo[1,2-a]indole-4,7-dione carbamate This compound was prepared by the procedure described in Example 1. From 72 mg of mitomycin A and excess 1-(2-aminoethyl)-2-nitroimidazole was obtained 60 mg (70% yield) of the desired product having a melting point of 83°–85° C. (decomposition) and providing the following analysis:

NMR (CDCl$_3$, TS): 'δ' values in ppm. Absence of the 6-methoxy peak at 4.02 and the appearance of new peaks at 3.4 (t,2), 4.6 (t,2), 7.3 (broad s,2) and 7.6 (s,1).

EXAMPLE 28

1,1a,2,8,8a,8b-Hexahydro-8-(hydroxymethyl)-8a-methoxy-5-methyl-6-[2-(4-hydroxyphenyl)ethylamino]-azirino[2',3':3,4]pyrrolo[1,2-a]indole-4,7-dione carbamate This compound was prepared by the procedure described in Example 1. From 130 mg of mitomycin A and 510 mg of tyramine was obtained 138 mg (81% yield) of the desired product having a melting point of 120°–125° C. (decomposition) and providing the following analysis:

NMR (CDCl$_3$, TS): 'δ' values in ppm. Absence of the 6-methoxy peak at 4.02 and the appearance of new peaks at 2.6 (t,2), 2.8 (t,2), 6.7 (d,2), 7.0 (d,2) and 8.0 (s,1).

EXAMPLE 29

1,1a,2,8,8a,8b-Hexahydro-8-(hydroxymethyl)-8a-methoxy-5-methyl-6-[2-(3,4-dihydroxyphenyl)ethylamino]-azirino[2',3':3,4]pyrrolo[1,2-a]indole-4,7-dione carbamate This compound was prepared by the procedure described in Example 1, except that 138 mg of sodium methoxide was added. From 110 mg of mitomycin A and 660 mg of 3-hydroxytyramine hydrobromide was obtained 60 mg (40% yield) of the desired product decomposing without melting above 125° C. and providing the following analysis:

NMR (CDCl$_3$, TS): 'δ' values in ppm. Absence of the 6-methoxy peak at 4.02 and the appearance of new peaks at 2.6 (t,2), 2.8 (t,2), 6.4–6.8 (m,3) and 8.3 (broad s,2).

EXAMPLE 30

1,1a,2,8,8a,8b-Hexahydro-8-(hydroxymethyl)-8a-methoxy-5-methyl-6-{2-[(5-nitro-2-pyridyl)amino]ethylamino)}-azirino[2',3':3,4]pyrrolo[1,2-a]indole-4,7-dione carbamate This compound was prepared by the procedure described in Example 1, except that the solvent was dichloromethane. From 50 mg of mitomycin A and 30 mg of 2-(2-aminoethylamino)-5-nitropyridine was obtained 40 mg (56% yield) of the desired product having a melting point of 76°–79° C. (decomposition) and providing the following analysis:

NMR (CDCl$_3$, TS): 'δ' values in ppm. Absence of the 6-methoxy peak at 4.02 and the appearance of new peaks at 3.3–4.0 (m,4), 6.2–6.7 (broad s,2), 8.1 (d,1), 8.2 (d,1) and 9.0 (s,1).

EXAMPLE 31

1,1a,2,8,8a,8b-Hexahydro-8-(hydroxymethyl)-8a-methoxy-5-methyl-6-[2-(1-piperazinyl)ethylamino]-azirino[2',3':3,4]pyrrolo[1,2-a]indole-4,7-dione carbamate This compound was prepared by the procedure described in Example 1, except that the solvent was dichloromethane. From 50 mg of mitomycin A and 20 mg of N-(2-aminoethyl) piperazine was obtained 23 mg (36% yield) of the desired product having a melting point of 138°–141° C. (decomposition) and providing the following analysis:

NMR (CDCl$_3$, TS): 'δ' values in ppm. Absence of new 6-methoxy peak at 4.02 and the appearance of new peaks at 1.6–2.1 (broad s,1), 2.2–2.6 (broad s,8), 2.6–2.8 (broad s,4) and 6.9 (t,1).

EXAMPLE 32

1,1a,2,8,8a,8b-Hexahydro-8-(hydroxymethyl)-8a-methoxy-5-methyl-6-[2-(2-pyridyl)ethylamino]-azirino[2',3':3,4]pyrrolo[1,2-a]indole-4,7-dione carbamate This compound was prepared by the procedure described in Example 1. From 70 mg of mitomycin A and 250 mg excess of 2-(2-aminoethyl)pyridine was obtained 51 mg (56% yield) of the desired product having a melting point of 64°–77° C. (decomposition) and providing the following analysis:

NMR (CDCl$_3$, TS): 'δ' values in ppm. Absence of the 6-methoxy peak at 4.02 and the appearance of new peaks at 2.8 (m,4), 7.0–7.8 (m,3) and 8.5 (d,1).

With specific reference to the compounds comprehended by formula IIIa, the above examples illustrate the following structural variations.

1. Compounds wherein Z is a hydroxy substituted 1-pyrrolidinyl radical represented by Example 1.
2. Compounds wherein Z is a lower alkyl substituted piperidyl radical represented by Example 2.
3. Compounds wherein Z is a 1-piperazinyl radical or an acetamino, acetyl, carbamido, cyano, carboxy lower alkylamino, di-lower alkoxy, nitro, sulfamyl or lower alkyl substituted anilino radical are represented, respectively, by Examples 3, 4, 5, 6, 7, 8, 9, 10, 11, 12, 13, 14, 15 and 16.
4. Compounds wherein Z is a radical of the formula

and wherein R$^1$ is a nitrogen containing heterocylic radical selected from the group consisting of amino substituted triazolyl, lower alkyl substituted isothiazolyl, benzothiazolyl and nitro and halo substituted derivatives of benzothiazolyl are represented, respectively, by Examples 17, 18, 19, 20 and 21.

5. Compounds wherein Z is a radical of the formula

and wherein R$^1$ is a substituted lower alkyl radical selected from the group consisting of amino lower alkyl, lower alkylamino lower alkyl, hydroxy lower alkylamino lower alkyl, hydroxy lower alkoxy lower alkyl, imidazolyl lower alkyl, nitro substituted imidazolyl lower alkyl, mono- and di-hydroxy phenyl lower alkyl, nitro substituted pyridylamino lower alkyl, piperazinyl lower alkyl and pyridyl ethyl are represented, respectively, by Examples 22, 23, 24, 25, 26, 27, 28, 29, 30, 31 and 32.

While none of the foregoing examples are illustrative of compounds wherein Y is other than hydrogen, compounds wherein Y is lower alkyl are nonetheless within the comprehension of the invention, reference being made to analogously substituted compounds of my aforesaid U.S. Pat. No. 4,268,676 and co-pending patent application Ser. Nos. 206,529 and 264,187.

Compounds according to the present invention are believed to possess anti-bacterial activity against gram-positive and gram-negative microorganisms in a manner similar to that observed for the naturally occurring mitomycins and are thus potentially useful as therapeutic agents in treating bacterial infections in humans and animals.

Usefulness of compounds of formula IIIa in the anti-neoplastic therapeutic methods of the invention is demonstrated by the results of in vivo screening procedures wherein the compounds are administered in varying dosage amounts to mice in which a P388 leukemic condition is induced. The procedures were carried out according to "Lymphocytic Leukemia P388 - Protocol 1.200", published in *Cancer Chemotherapy Reports*, Part 3, Vol. 3, No. 2, page 9 (September, 1972). Briefly put, the screening procedures involved administration of the test compound to CDF$^1$ female mice previously infected with 10$^6$ ascites cells implanted intraperitoneally. Test compounds were administered on the first day of testing only, and the animals were monitored for vitality, inter alia, over a 35-day period.

Results of screening of compounds of Examples 1 through 32 are set forth in Table I below. Data given includes optimal dose ("O.D."), i.e., that dosage in mg/kg of body weight of the animal at which the maximum therapeutic effects are consistently observed. Also included is the median survival time ("MST") expressed as the MST of the test animals compared to the MST of controls × 100 ("% T/C"). Within the context of the in vivo P388 procedure noted above, a % T/C value of 125 or greater indicates significant anti-neoplastic therapeutic activity. The lowest dose in mg/kg of body weight at which the 125% T/C value is obtained is known as the minimum effective dose ("MED"). These doses also are listed in Table I. It is worthy of note that the exceptionally high MST values obtained in the P388 screenings reported in Table I are also indicative of the absence of substantial toxicity of the compounds at the dosages indicated.

TABLE 1

| Example No. | Optimal Dose mg/kg | MST as % T/C | MED |
|---|---|---|---|
| 1 | 25.6 | 163 | 0.8 |
| 2 | 25.6 | 238 | <0.2 |
| 3 | 12.8 | 200 | 0.2 |
| 4 | 25.6 | >333 | <0.2 |
| 5 | 25.6 | 231 | 0.2 |
| 6 | 6.4 | 167 | 0.4 |
| 7 | 25.6 | 194 | 1.6 |
| 8 | 3.2 | 150 | 0.8 |
| 9 | 12.8 | 172 | <0.2 |
| 10 | 25.6 | 322 | 0.8 |
| 11 | 12.8 | >333 | 0.2 |
| 12 | 6.4 | 161 | 0.4 |
| 13 | 3.2 | 172 | >0.2 |
| 14 | 25.6 | 225 | 0.2 |
| 15 | 12.8 | 167 | 0.4 |
| 16 | 12.8 | 181 | 0.4 |
| 17 | 12.8 | 181 | 1.6 |
| 18 | 25.6 | 169 | 0.8 |
| 19 | 25.6 | 150 | 12.8 |
| 20 | 25.6 | 128 | 25.6 |
| 21 | 25.6 | 144 | 1.6 |
| 22 | 3.2 | 178 | 0.4 |
| 23 | 25.6 | 133 | 12.8 |
| 24 | 12.8 | 133 | 12.8 |
| 25 | 25.6 | 181 | 0.4 |
| 26 | 25.6 | 163 | 1.6 |
| 27 | 25.6 | 150 | 3.2 |
| 28 | 25.6 | 218 | 1.6 |
| 29 | 12.8 | 139 | 12.8 |
| 30 | 12.8 | 144 | 6.4 |
| 31 | 25.6 | 138 | 12.8 |
| 32 | 25.6 | >375 | 0.2 |

Clearly among the most preferred compounds employed as antineoplastic agents according to the invention are those exhibiting more than twice the relative life-extending capacity generally characterized as evidencing significant therapeutic potential, i.e., those having an MST % T/C value greater than 2×125. The class of such compounds is seen to include the compounds of Examples 4, 10, 11 and 32.

As may be noted from Table I, initial single dosages of as little as 0.2 mg/kg showed substantial long term antineoplastic activity. Accordingly, the methods of the invention may involve therapeutic administration of unit dosages of as little as 0.001 mg or as much as 5 mg, preferably from 0.004 mg to 10 mg, of the compounds as the active ingredient in a suitable pharmaceutical preparation. Such preparations may be administered in a daily regimen calling for from 0.1 mg to 100 mg per kg, preferably from about 0.2 to about 51.2 mg per kg, of the body weight of the animal suffering from neoplastic disease. It is preferred that the compounds be administered parenterally. Pharmaceutical compositions suitable for use in practice of methods of the invention may comprise simple water solutions of one or more of the compounds of formula IIIa, but may also include well known pharmaceutically acceptable diluents, adjuvants and/or carriers such as saline suitable for medicinal use.

Further aspects and advantages of the present invention are expected to occur to those skilled in the art upon consideration of the foregoing description and consequently only such limitations as appear in the appended claims should be placed thereon.

What is claimed is:

1. Compounds of the formula

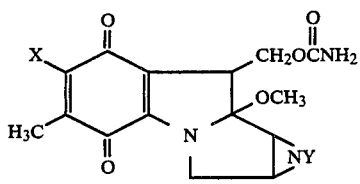

III wherein: Y is hydrogen or lower alkyl; and X is an anilino radical substituted with an acetamino, acetyl, carbamido, cyano or carboxy group.

2. The compounds according to claim 1 named:
1,1a,2,8,8a,8b-hexahydro-8-(hydroxymethyl)-8a-methoxy-5-methyl-6-[4-(acetylamino)anilino]-azirino[2',3':3,4]pyrrolo[1,2-a]indole-4,7-dione carbamate;
1,1a,2,8,8a,8b-hexahydro-8-(hydroxymethyl)-8a-methoxy-5-methyl-6-[3-acetylamino)anilino]-azirino[2',3':3,4]pyrrolo[1,2-a]indole-4,7-dione carbamate;
1,1a,2,8,8a,8b-hexahydro-8-(hydroxymethyl)-8a-methoxy-5-methyl-6-(4-acetylanilino)-azirino[2',3':3,4]pyrrolo[1,2-a]indole-4,7-dione carbamate;
1,1a,2,8,8a,8b-hexahydro-8-(hydroxymethyl)-8a-methoxy-5-methyl-6-[4-(1-ureido)anilino]-azirino[2',3':3,4]pyrrolo[1,2-a]indole-4,7-dione carbmate;
1,1a,2,8,8a,8b-hexahydro-8-(hydroxymethyl)-8a-methoxy-5-methyl-6-(4-cyanoanilino)-azirino[2',3':3,4]pyrrolo[1,2-a]indole-4,7-dione carbamate;
1,1a,2,8,8a,8b-hexahydro-8-(hydroxymethyl)-8a-methoxy-5-methyl-6-(3-cyanoanilino)-azirino[2',3':3,4]pyrrolo[1,2-a]indole-4,7-dione carbamate; and
1,1a,2,8,8a,8b-hexahydro-8-(hydroxymethyl)-8a-methoxy-5-methyl-6-[4-(N-glycyl)anilino]-azirino[2',3':3,4]pyrrolo[1,2-a]indole-4,7-dione carbamate.

3. Compounds of the formula

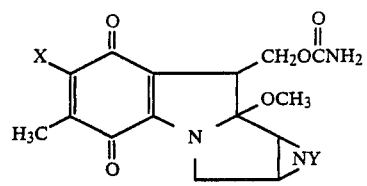

III wherein: Y is hydrogen or lower alkyl; and X is a radical of the formula,

wherein R is hydrogen or lower alkyl and R' is a nitrogen containing heterocyclic radical selected from the group consisting of amino substituted triazolyl, and benzothiazolyl substituted with a nitro or halo group.

4. The compounds according to claim 3 named:
1,1a,2,8,8a,8b-hexahydro-8-(hydroxymethyl)-8a-methoxy-5-methyl-6-[(5-amino-1,2,4-triazol-3-yl)amino]azirino[2',3':3,4]pyrrolo[1,2-a]indole-4,7-dione carbamate;
1,1a,2,8,8a,8b-hexahydro-8-(hydroxymethyl)-8a-methoxy-5-methyl-6-[(6-nitrobenzothiazol-2-yl)amino]-azirino[2',3':3,4]pyrrolo[1,2-a]indole-4,7-dione carbamate;
1,1a,2,8,8a,8b-hexahydro-8-(hydroxymethyl)-8a-methoxy-5-methyl-6-[(4-chlorobenzothiazol-2-yl)amino]-azirino[2',3':3,4]pyrrolo[1,2-a]indole-4,7-dione carbamate.

5. A compound of the formula,

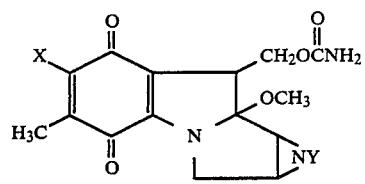

III wherein Y is hydrogen or lower alkyl; and X is an anilino radical substituted with a nitro group.

6. The compound according to claim 5 named:
1,1a,2,8,8a,8b-hexahydro-8-(hydroxymethyl)-8a-methoxy-5-methyl6-(4-nitroanilino)-azirino[2',3':3,4]-pyrrolo[1,2-a]indole-4,7-dione carbamate.

7. A compound of the formula,

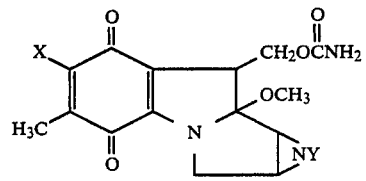

III wherein Y is hydrogen or lower alkyl and X is a radical of the formula,

wherein R is a hydrogen or a lower alkyl and R' is isothiazolyl having a lower alkyl substituent.

8. The compound according to claim 7 named: 1,1a,2,8,8a,8b-hexahydro-8-(hydroxymethyl)-8a-methoxy-5-methyl-6-[(3-methylisothiazol-5-yl)amino]-azirino[2',3':3,4]pyrrolo[1,2-a]indole-4,7-dione carbamate.

9. Compounds of the formula

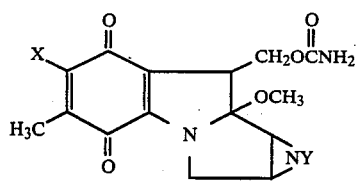

III wherein: Y is hydrogen or lower alkyl; and X is a radical of the formula:

wherein R is hydrogen and R' is a substituted lower alkyl radical selected from the group consisting of an amino substituted lower alkyl, hydroxy substituted lower alkylamino lower alkyl, an hydroxy substituted lower alkoxy lower alkyl, an imidazolyl substituted lower alkyl, a nitro substituted imidazolyl substituted lower alkyl, a mono- or di-hydroxy substituted phenyl lower alkyl, and a nitro substituted pyridylamino lower alkyl.

10. The compounds according to claim 9 named:
1,1a,2,8,8a,8b-hexahydro-8-(hydroxymethyl)-8a-methoxy-5-methyl-6-[(2-aminoethyl)amino]-azirino[2',3':3,4]pyrrolo[1,2-a]indole-4,7-dione carbamate;

1,1a,2,8,8a,8b-hexahydro-8-(hydroxymethyl)-8a-methoxy-5-methyl-6-[2-(2-hydroxyethylamino)ethylamino]azirino[2',3':3,4]pyrrolo[1,2-a]indole-4,7-dione carbamate;

1,1a,2,8,8a,8b-hexahydro-8-hydroxymethyl)-8a-methoxy-5-methyl-6-[2-(2-hydroxyethoxy)ethylamino]-azirino[2',3':3,4]pyrrolo[1,2-a]indole-4,7-dione carbmate;

1,1a,2,8,8a,8b-hexahydro-8-(hydroxymethyl)-8a-methoxy-5-methyl-6-[2-(4-imidazolyl)ethylamino]-azirino[2',3':3,4]pyrrolo[1,2-a]indole-4,7-dione carbamate;

1,1a,2,8,8a,8b-hexahydro-8-(hydroxymethyl)-8a-methoxy-5-methyl-6-[(2-nitro-1-imidazolyl)ethylamino]-azirino(2',3':3,4]pyrrolo[1,2-a]indole-4,7-dione carbamate;

1,1a,2,8,8a,8b-hexahydro-8-(hydroxymethyl)-8a-methoxy-5-methyl-6-[2-(4-hydroxyphenol)ethylamino]-azirino[2',3':3,4]pyrrolo[1,2-a]indole-4,7-dione carbamate;

1,1a,2,8,8a,8b-hexahydro-8-(hydroxymethyl)-8a-methoxy-5-methyl-6-[2-(3,4dihydroxyphenyl)ethylamino]azirino[2',3':3,4]pyrrolo[1,2-a]indole-4,7-dione carbamate;

1,1a,2,8,8a,8b-hexahydro-8-(hydroxymethyl)-8a-methoxy-5-methyl-6-2-[(5-nitro-2-pyridyl)amino]ethylaminoazirino[2',3':3,4]pyrrolo[1,2-a]indole-4,7-dione carbamate.

* * * * *